US008996136B2

(12) United States Patent
Weiss

(10) Patent No.: US 8,996,136 B2
(45) Date of Patent: Mar. 31, 2015

(54) IMPLANTABLE DEVICE WITH AN ELONGATED ELECTRIC CONDUCTOR

(75) Inventor: Ingo Weiss, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 782 days.

(21) Appl. No.: 13/301,694

(22) Filed: Nov. 21, 2011

(65) Prior Publication Data

US 2012/0157814 A1    Jun. 21, 2012

Related U.S. Application Data

(60) Provisional application No. 61/425,249, filed on Dec. 21, 2010.

(51) Int. Cl.
*A61N 1/08* (2006.01)
*A61N 1/06* (2006.01)
*A61N 1/37* (2006.01)
*A61B 18/14* (2006.01)
*A61N 1/05* (2006.01)

(52) U.S. Cl.
CPC .......... *A61N 1/3718* (2013.01); *A61B 18/1492* (2013.01); *A61N 1/056* (2013.01); *A61N 2001/086* (2013.01)
USPC .......................................... 607/122; 600/374

(58) Field of Classification Search
CPC ... A61N 1/056; A61N 1/08; A61N 2001/086; A61B 18/1492
USPC .................................. 600/374; 607/119, 122
See application file for complete search history.

(56) References Cited

U.S. PATENT DOCUMENTS

2008/0147154 A1*   6/2008   Gray et al. ..................... 607/115

FOREIGN PATENT DOCUMENTS

| EP | 1632265 A1 | 3/2006 |
|---|---|---|
| WO | 2006/083668 A2 | 8/2006 |
| WO | 2008/073445 A2 | 6/2008 |

OTHER PUBLICATIONS

European Search Report dated Apr. 24, 2012, 5 pages.

* cited by examiner

*Primary Examiner* — Tammie K Heller
(74) *Attorney, Agent, or Firm* — ARC IP Law, PC; Joseph J. Mayo

(57) ABSTRACT

An implantable medical device, which is connected or is to be connected to at least two elongated electric function conductors for the transmission of treatment signals or diagnostic signals or both, and at least one electrode pole connected to at least one of the function conductors, via which electrode pole electric current can be delivered in the case of use to surrounding tissue of the body or with which electric potentials can be sensed in the surrounding tissue or both. Includes a wave transfer module connected to the function conductor and which is embodied to transform waves arriving via a function conductor and to switch them as transformed waves onto another function conductor or the same function conductor in such a controlled manner that the waves are destructively superimposed at the electrode pole.

12 Claims, 3 Drawing Sheets

IMPLANTABLE DEVICE WITH AN ELONGATED ELECTRIC CONDUCTOR

This application claims the benefit of U.S. Provisional Patent Application 61/425,249 filed on 21 Dec. 2010, the specification of which is hereby incorporated herein by reference.

BACKGROUND OF THE INVENTION

1. Field of the Invention

At least one embodiment of the invention relates to a permanently or temporarily implantable device having an elongated electric conductor.

2. Description of the Related Art

Devices of this type, for example, electrode lines for electrostimulation, have the disadvantage that the electric conductor thereof can heat up in an MRI scanner because the alternating magnetic fields prevailing in the MRI scanner induce not inconsiderable electric currents in the electric conductor. Induced currents of this type can also be emitted via electrode poles of the electrode line to surrounding tissue and thus, for example, lead to undesirable heating of the tissue. For this reason, nowadays patients with cardiac pacemakers usually cannot be examined, or can be examined only to a limited extent, in an MRI scanner.

At least one stimulation electrode line is typically connected to implantable cardiac pacemakers or defibrillators (also referred to below jointly as cardiac stimulators or IPG (implantable pulse generator)), which stimulation electrode line has a standardized electrical connection at its proximal end provided for connection to the cardiac pacemaker or defibrillator and has one or more electrode poles on its distal end provided for placement in the heart. An electrode pole of this type is used to deliver electric pulses to the tissue (myocardium) of the heart or to sense electric fields, in order to be able to sense an activity of a heart within the scope of the so-called sensing. For these purposes, electrode poles typically form electrically conductive surface sections of an electrode line. Electrode poles are typically provided as an annular electrode in the form of a ring around the electrode line or in the form of a point electrode or tip electrode at the distal end of the electrode line. The electrode poles are connected in an electrically conductive manner via one or more electric conductors to contacts of the electric connection of the electrode line at the proximal end thereof. Thus one or more electric conductors run between the contacts of the electrical connection the electrode lines at the proximal end thereof and the electrode poles at the distal end of the electrode line, which conductors electrically connect one or more of the electrode poles to one or more of the contacts. These electric conductors can be used, on the one hand, to transmit stimulation pulses to the electrode poles and, on the other hand, to transmit electric signals recorded by means of the electrode poles to the proximal end of the electrode line and are also respectively referred to as a function line in the course of the further description. Function lines of this type are electric conductors necessary for the functions of the respective electrode line and as such are exposed to the risk of electric currents being induced in them through external alternating magnetic fields, which currents can lead, for example, to an undesirable heating up of the function lines or of the electrode poles connected to them or which can lead to the delivery of corresponding currents via the electrode poles to surrounding tissue and thus to a heating of the surrounding tissue.

BRIEF SUMMARY OF THE INVENTION

At least one embodiment of the invention is based on the object of creating a device that solves the problem described above.

According to at least one embodiment of the invention, this object is attained by a temporarily or permanently implantable medical device, which is connected or is to be connected to at least two elongated electric function conductors for the transmission of treatment signals or diagnostic signals or both, and at least one electrode pole connected to at least one of the function conductors, via which electrode pole electric current can be delivered in the case of use to surrounding tissue of the body or with which electric potentials in the case of use can be sensed in the surrounding tissue or both.

According to at least one embodiment of the invention, the medical device has a wave transfer module that is connected or is to be connected to the function conductor and which is embodied to transform waves arriving via a function conductor and to switch them as transformed waves onto another function conductor or the same function conductor in such a controlled manner that the waves are destructively superimposed at the electrode pole.

A medical device for which the invention is particularly relevant is an electrode line, e.g., for a cardiac stimulator, in which the function conductors are electric conductors of the electrode line, wherein the electrode line has electrode poles, which are electrically connected via the function connectors to the wave transfer module.

The medical device, for example, an implantable cardiac stimulator connected to an electrode line, can have a housing, which is embodied in an electrically conductive manner or has an electrode pole via which electric current in case of use can be transmitted to surrounding body tissue or with which electric potentials in surrounding tissue can be sensed or both.

Preferably, the medical device has an interference field recognition device, which is embodied to detect a presence of strong electromagnetic fields and in the case of the presence to generate a corresponding output signal, and which is connected to a control unit for controlling the wave transfer module.

The interference field recognition device can have a temperature sensor, which is arranged such that it can detect a heating of an electrode pole. In this manner, the interference field recognition device detects a heating as the result of high-frequency interference fields and thus interference fields indirectly via their effect. The temperature sensors are located at the electrode poles or other locations that can heat up due to the interactions with electromagnetic fields.

Alternatively or additionally, the interference field recognition device can have a sensor for currents or voltages induced in a function conductor and thus be embodied to directly detect induced currents or voltages.

According to a preferred embodiment, the wave transfer module has a delay line, which delays and or damps electromagnetic waves, so that in the case of operation a transformed wave is produced, which is destructively superimposed with an induced wave on the same or a different function conductor and in this manner compensates for the induced wave. The delay line can have an impedance that causes this effect.

According to an embodiment variant, the delay line is realized by one or more, preferably discrete electronic components from a group that comprises coils, capacitors, ohmic resistances and transducers. These form, for example, an LC circuit, optionally also with an ohmic resistance, in order to adjust the damping.

Additionally or alternatively, the delay line can have three-dimensional structures which, due to their physical properties, have a wave-delaying and/or damping effect. Three-dimensional structures of this type are not necessarily discrete electronic components but e.g., a waveguide, a coaxial line, a strip line, with optionally lossy materials in order to adjust the damping. The wave transfer module is hereby preferably adjustable with respect to its effect, in particular with respect to its delaying effect and/or its damping effect, e.g., in that the adjustable elements are operated electrically, mechanically, optically, etc. The adjustment of the controllable delay lines can also be carried out by an external programming device.

Expediently, the wave transfer module has a switching unit which is arranged and embodied to switch transformed waves on a function conductor determined by the switching unit or not. This makes it possible to use the wave transfer module only when it is necessary and furthermore to adapt it to the respective case of use. The adjustment of the switching unit can also be carried out by an external programming device.

According to a preferred embodiment variant, a delay line of the wave transfer module connects at least two function conductors, wherein the connection is to be produced via the switching unit. The switching unit can have the form of a switching matrix in which every cross point in the switching matrix is occupied by a switch.

According to a further embodiment, the medical device can have a terminal impedance unit and the wave transfer module can have a switching unit, which is arranged and embodied to connect a function conductor to a terminal impedance unit. The terminal impedance can cause a phase shift of a wave on a function conductor and thus likewise contribute to the desired effect of a wave cancellation. For this purpose, preferably at least one impedance value of the terminal impedance unit can be electrically, mechanically or optically controlled. The terminal impedances can be realized discretely or physically. The adjustment of the controllable terminal impedances can also be carried out through an external programming device.

The control device is preferably embodied to control the controllable delay lines and/or the controllable terminal impedances and/or the switching unit depending on an output signal of the interference field recognition device such that in case of use a heating induced by interference fields at the electrode poles is minimized.

Particularly preferably, a battery operated electronic implant with

An electrically conductive housing or a housing with at least one electrode pole, Electric function conductors that connect the electrode poles of electric feed-through of the implant in order to be able to conduct electric signals from the respective electrode pole into the implant, An interference field recognition device for detecting the presence of strong electro-magnetic fields, in particular MRI fields, and A wave transfer module, which is controlled by the interference field recognition device via a control device and transforms waves reaching the implant via at least one function conductor and switches them onto at least one other function conductor such that the waves are destructively superimposed on the distal electrode poles so that there the heating due to MRT is minimized.

Alternatively to a controllable terminal impedance, a controllable generator can also be provided which is embodied to actively feed a compensation signal into a function conductor. The compensation signal to be fed in has the same frequency as the interference signal and a certain phase position, wherein the frequency is determined via the interference field recognition device and the phase position and amplitude are adjusted after evaluation of the temperature signals such that the interference field induced heating at the electrode poles (optionally generally the temperature measurement points) is minimized.

In addition to the embodiments described herein other alternative embodiments may include some or all of the disclosed features.

BRIEF DESCRIPTION OF THE DRAWINGS

At least one embodiment of the are now explained in more detail with reference to the Figures. The figures show the following.

DETAILED DESCRIPTION OF THE INVENTION

The implantable cardiac stimulator 10 can be a cardiac pacemaker or a cardioverter/defibrillator (ICD). In the exemplary embodiment shown, the cardiac stimulator 10 is a ventricular cardiac pacemaker and defibrillator. Other known cardiac stimulators are dual-chamber cardiac pacemakers for the stimulation of the right atrium and of the right ventricle or biventricular cardiac pacemakers that, in addition to the right ventricle, can also stimulate the left ventricle.

Stimulators of this type typically have a housing 12, which is generally composed of metal and is thus electrically conductive and can be used as a large-area electrode pole. A terminal housing 14 is typically attached to the outside of the housing 12, which terminal housing is also referred to as a header. A header of this type typically has female contacts to accommodate plug contacts. The female contacts have electric contacts 16, which are connected via corresponding conductors to an electronic system arranged in the housing 12 of the cardiac stimulator 10.

Figure 1:
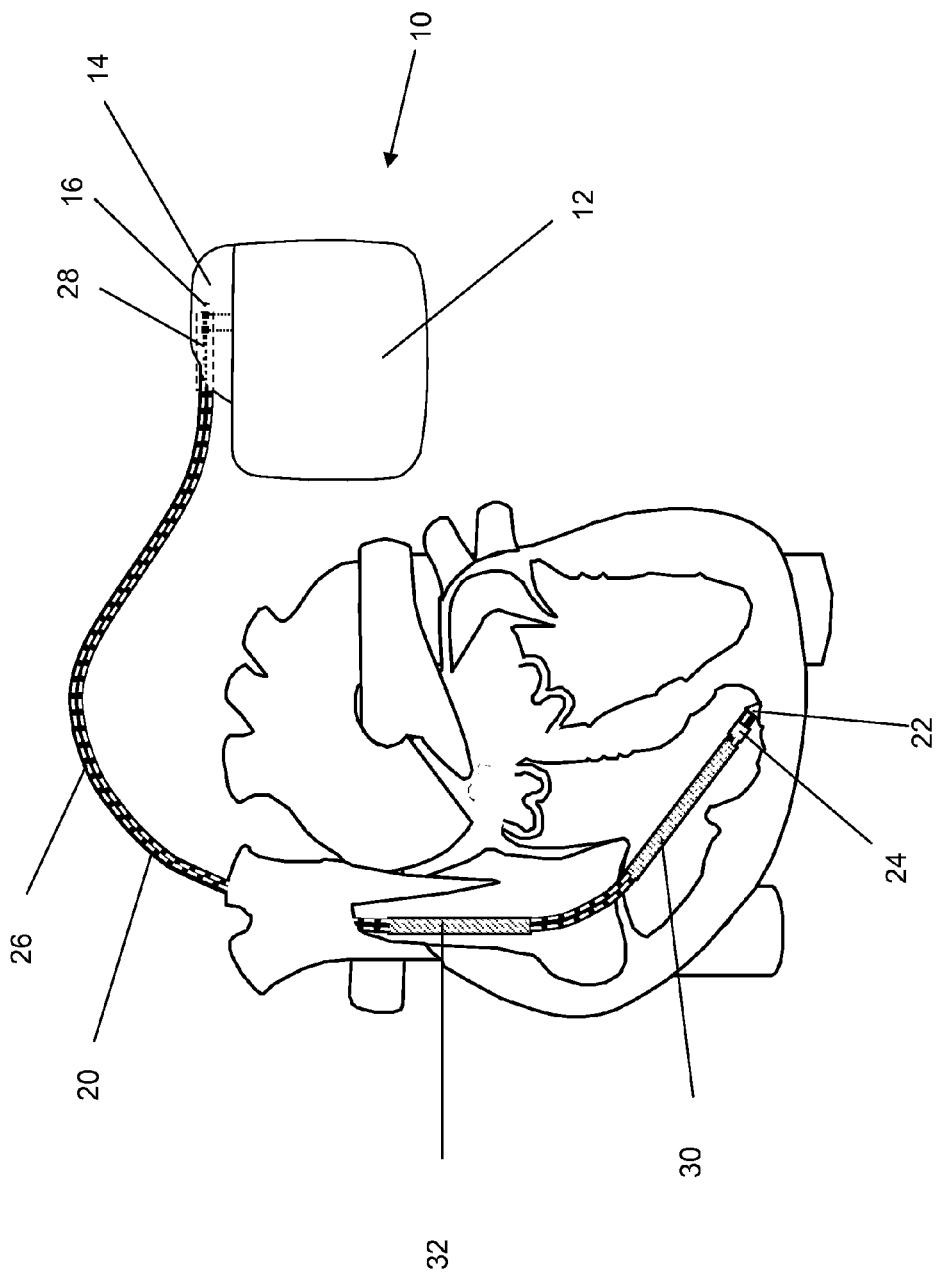
FIG. 1 shows as implantable medical devices an implantable cardiac stimulator 10 and an implantable electrode line 20 connected thereto.

In one or more embodiments, the electrode line 20 also represents an implantable medical device. Electrode poles in the form of a point electrode or tip electrode 22 and an annular electrode 24 arranged in their vicinity are arranged in a manner known per se at the distal end of the electrode line 20. The electrode poles 22 and 24 are embodied such that, depending on the function of a cardiac stimulator to which the electrode line 20 is connected, are used to sense electrical potentials of the cardiac tissue (myocardium) or are embodied to transmit electrical signals, for example, to deliver stimulation pulses to the cardiac tissue surrounding them. FIG. 1 shows how the electrode poles, that is, the tip electrode 22 and the annular electrode 24, in case of use the electrode line 20, are located in the apex of a right ventricle of a heart.

The tip electrode 22 as well as the annular electrode 24 are electrically connected via respectively at least one electric conductor 26 to a plug contact 28 at the proximal end of the electrode line 20. The plug contact 28 has electrical contacts that correspond to the electrical contacts 16 of the female contact in the terminal housing 14 of the implantable cardiac stimulator. The electric conductors 26 in the electrode line 20 can be embodied as approximately elongated cable pull conductors or as helically coiled conductors. Conductors of this type, which connect the functional electrode poles to electric contacts of the plug contact at the proximal end of the electrode line 20 in an electrically conductive manner, are also referred to as function conductors within the scope of this text, since they, for example, transmit electric signals for the purpose of treatment from the plug contact to the respective electrode pole or guide signals representing sensed electric potentials from the respective electrode pole to the plug contact and thus serve the elementary function of the medical device.

The electric conductors 26, which connect the electrode poles 22 and 24 respectively to the electric contacts of the plug connector 28 of the electrode line 20, are surrounded by an insulating sheath over the major part of their length, so that an electric contact to the tissue of the heart is produced in targeted manner via the electrode poles.

In addition to the electrode poles 22 and 24, which are typically used for the (in this case ventricular) stimulation of the cardiac tissue, the electrode line 20 also has two larger-area electrode poles 30 and 32, which serve as defibrillation electrodes and are formed by at least one uninsulated helically coiled wire.

It should be pointed out that within the scope of this exemplary embodiment the invention is explained on the basis of a right ventricular cardiac pacemaker and defibrillator. However, an ablation electrode line, for example, can basically also be used as a medical device for the purposes of the invention, which ablation electrode line in the case of use likewise projects into the heart of a patient and which is controlled by a device arranged outside the patient and is connected thereto for this purpose.

Figure 2:
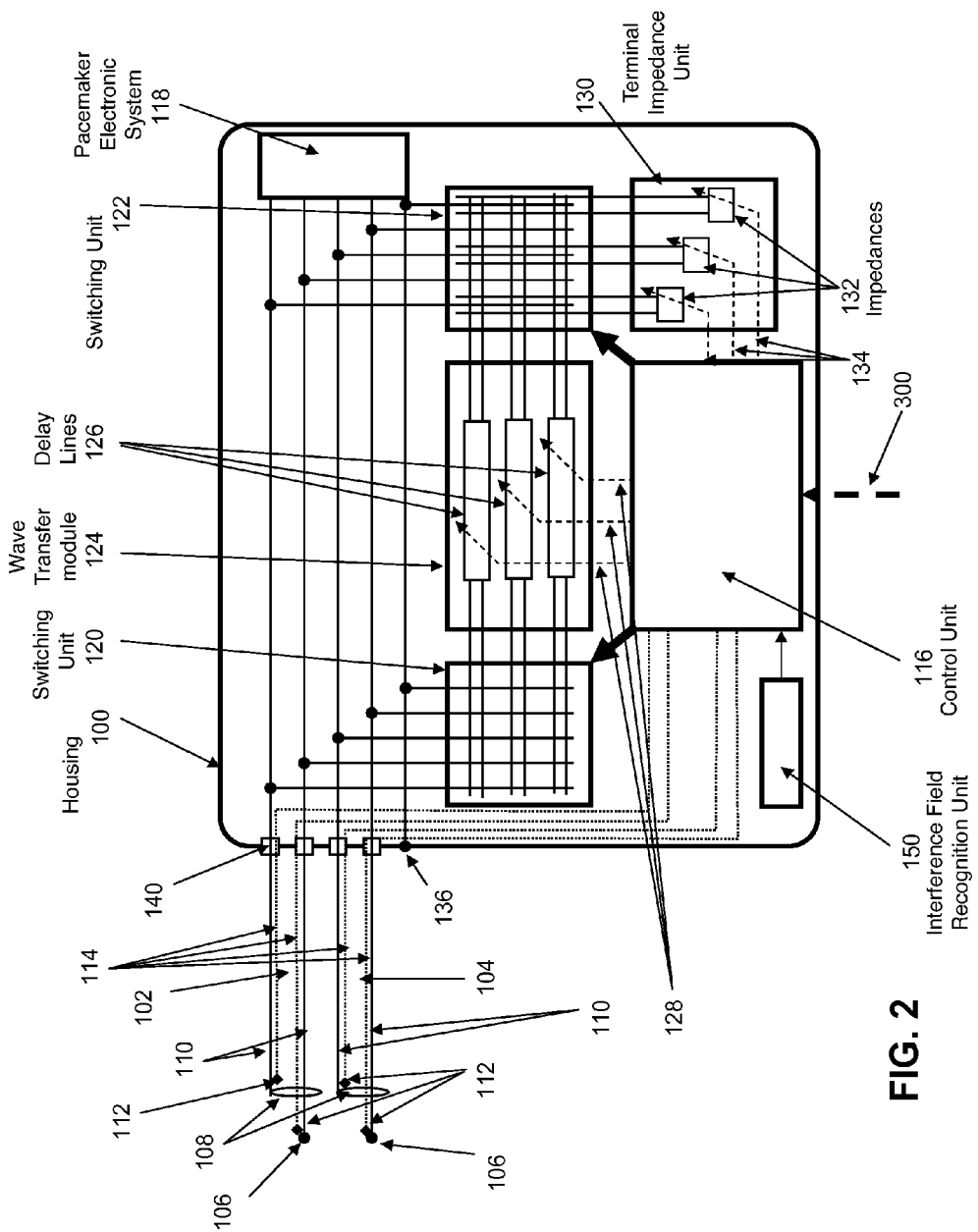
FIG. 2 shows in very diagrammatic representation the inner structure of a cardiac stimulator according to the invention.

FIG. 2 shows a diagrammatic representation of the inner structure of a medical device according to an embodiment the invention. The medical device has an electrically conductive housing 100, which corresponds to the housing 12 from FIG. 1. Two electrode lines 102 and 104, which respectively have a tip electrode 106 and an annular electrode 108, are connected to the housing. Each of the tip electrodes 106 and of the annular electrodes 108 respectively forms an electrode pole. Each electrode pole is connected via a separate feed line 110 to an electronic system in the interior of the housing 100. The feed lines 110 respectively form a function conductor. Temperature sensors 112 are respectively arranged in the immediate vicinity of the electrode poles 106 and 108, which are connected via signal lines 114 to a control unit 116 in the interior of the housing 100.

Instead of the temperature sensors 112, other sensors can also be for detecting electromagnetic interference fields or currents or voltages induced into the feed lines 110.

The feed lines 110 (function conductors) and the signal lines 114 are guided into the housing 100 via plug connectors not shown in FIG. 2 and via housing feed-throughs 140. The function conductor 110 is thereby connected to the typical components of a cardiac stimulator as well as sensing units or stimulation units. This is shown overall in FIG. 2 by the block 118 which represents the sensory and therapeutic cardiac pacemaker electronic system.

FIG. 2 shows that the function conductors 110 on the one hand are guided to the cardiac pacemaker electronic system 118 and on the other hand to switching units 120 and 122, which are embodied as switching matrices. A wave transfer module 124 is connected to the switching matrices 120 and 122, which wave transfer module has (in the case shown three) adjustable delay lines 126. The delay lines 126 are adjustable with respect to their delaying effect and/or their damping effect. For this purpose they are connected via control lines 128 to the control unit 116. In this manner they can be received by the control unit 116 depending on the signals that the control unit 116 receives via the signal lines 114 from the sensors 112 in the electrode lines 102 and 104. Concretely, the control device 116 is embodied to receive the switching matrices 120 and 122 as well as the delay lines 126 depending on the signals received via the signal lines 114 such that the signals entering via the signal lines 114 as far as possible do not show any heating of the electrode poles 106 and 108. In this context, the control unit 116 can also be seen as an operator control.

The latter effect is obtained with the aid of the adjustable delay lines 126 in that waves entering via the function conductors 110 are switched on the adjustable delay lines 126 and the delay lines 126 are adjusted such that the waves are transformed and are switched on the same or different function conductors in a manner such that they are destructively superimposed with induced waves and thus cancel the effect of the induced waves.

A terminal impedance unit 130, which in the concrete case has three adjustable terminal impedances 132, also alternatively or additionally serves this purpose. The adjustable impedances 132 can be adjusted by the control unit 116 via control lines 134. Through the adjustable terminal impedances 132, the reflection of the waves on the function conductors 110 at the proximal ends thereof defined by the terminal units can be adjusted with respect to phase position and damping in order in this manner to likewise achieve a destructive superposition of waves in the region of the electrode poles of the respective function conductors.

Instead of the terminal impedance unit 130, a compensation signal generator can also be provided, which generates compensation signals actively and controlled by the control unit 116 and feeds them into the respective function conductor.

It should be pointed out that the housing 100 of the cardiac stimulator represents a pole of its own, which likewise is electrically connected (see reference number 136) to the switching matrices 120 and 122 as well as the cardiac stimulator electronic system 118.

The control unit and thus the behavior of the switching units 120 and 122 as well as the adjustments of the delay lines 126 and of the terminal impedances 132 can be programmed externally. This is indicated by the arrow 300.

Figure 3:
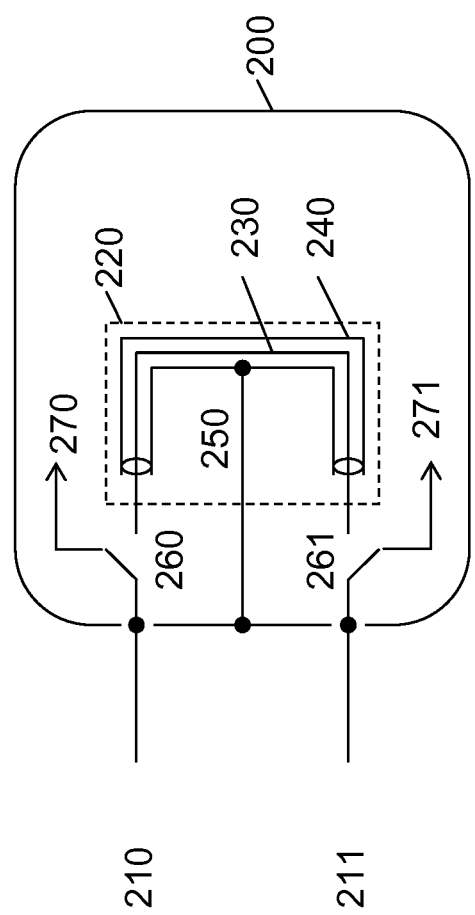
FIG. 3 shows in very diagrammatic representation a structure of a delay line.

The structure of an exemplary delay line is shown diagrammatically in FIG. 3. In FIG. 3 the reference numbers are used as follows:

200: Conductive implant housing
210: Line of an electrode
211: Line of an electrode (the same electrode as 110 or a different one)
220: Wave transfer module
230: Conductor of the delay line
240: Reference conductor of the delay line
250: Connection of the reference conductor of the delay line to the implant housing
260, 261: Switch
270, 271: Connection to the electronic system Upon recognition of a strong electromagnetic field (in particular HF fields, such as occur in MR scanners and which represent a risk potential for patient and implant) by the temperature sensors 112 and the control unit 116, which in this context form a interference field recognition unit, the switching of the electrode inputs in the implant is automatically reconfigured. This is caused by the control unit 116, which is correspondingly programmed or structured. This switching is carried out only temporarily while the interference occurs, in the day-to-day operation of the implant the high-resolution and broadband signal recording, in particular also the impedance determination for a hemodynamic sensor, is not impaired. The electrode lines then run directly (as usual) into the electronic system 118 of the cardiac stimulator. In a preferred realization, during the interference and switching according to the invention with delay lines, the electronic system 118 is switched away at some or all inputs. A switch provided for this purpose and controlled by the control unit 116 is not shown in FIG. 2.

FIG. 2 shows an optional additional interference field recognition unit 150 which reacts to interference fields in general and in this case actives the control unit 116, as described above, for the duration of the interference fields or for a predetermined period.

In a preferred implementation, the coupling of the feed lines is carried out by means of the switching matrices 120 and 122 such that, e.g., the center conductor of a first electrode is switched (coaxially) on the outer conductor of a second electrode. In a further realization, at the same time the center conductor of the second electrode is switched on the outer conductor of the first electrode (cross connection). In a further realization, the delay is thereby virtually 0 seconds, i.e. it is switched directly without the use of delay lines.

In the interconnection of the electrodes, for optimization with respect to heating it is additionally ensured that the areas enclosed between the electrodes are minimal. The currents induced by MRI gradient fields are thus minimized and the risk of undesirable cardiac stimulation (induced by the MR scanner) is reduced. In particular, a connection is not produced to the housing potential.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An implantable medical device comprising:
   a plurality of function conductors comprising at least two elongated electric function conductors that are configured to transmit treatment signals or sense diagnostic signals, or both;
   at least one electrode pole connected to at least one elongated electric function conductor of the plurality of function conductors, wherein electric currents are delivered to surrounding tissue of a body or with which electric potentials are sensed in the surrounding tissue or both via the at least one electrode pole;
   a wave transfer module comprising
      a delay line that is adjustable and controllable, and
      a switching unit configured to switch transformed waves on a particular function conductor determined by the switching unit;
         wherein said switching unit is a switching matrix; and,
         wherein said delay line connects at least two function conductors of the plurality of function conductors via said switching unit;
   wherein said wave transfer module is configured to
      connect to the at least one elongated electric function conductor,
      transform waves arriving via the at least one elongated electric function conductor, and
      switch the waves arriving as transformed waves onto the delay line, wherein the delay line is adjusted such that the waves are transformed and switched onto another function conductor of the plurality of function conductors or onto the at least one elongated electric function conductor in a controlled manner such that the waves are destructively superimposed at the at least one electrode pole.

2. The implantable medical device according to claim 1, wherein the function conductors are electric conductors of an electrode line, which has electrode poles, which are electrically connected via the function conductors to the wave transfer module.

3. The implantable medical device according to claim 1, further comprising a housing, wherein said housing is electrically conductive or is coupled with the at least one electrode pole.

4. The implantable medical device according to claim 1, further comprising a control unit and an interference field recognition device connected to said control unit, wherein said interference field recognition device is configured to detect a presence of strong electromagnetic fields and generate a corresponding output signal, and wherein the control unit is configured to control the wave transfer module.

5. The implantable medical device according to claim 4, wherein the interference field recognition device comprises a temperature sensor, which is arranged such that it can detect a heating of the at least one electrode pole.

6. The implantable medical device according to claim 4, wherein the interference field recognition device comprises a sensor configured to detect currents or voltages induced in the function conductors.

7. The implantable medical device according to claim 4, wherein the wave transfer module is adjustable;
   wherein the implantable medical device further comprises a terminal impedance unit;
   wherein said switching unit is configured to connect the particular function conductor to said terminal impedance unit;
   wherein said terminal impedance unit comprises at least one impedance value that is controllable; and
   wherein the control unit is configured to control one or more of said controllable delay line, said controllable at least one terminal impedance, and the switching unit, depending on an output signal from the interference field recognition device in order to minimize heating induced by interference fields at the electrode poles.

8. The implantable medical device according to claim 1, wherein the delay line comprises one or more coils, capacitors, ohmic resistances and transducers or any combination thereof.

9. The implantable medical device according to claim 1, wherein the delay line comprises three-dimensional structures having a wave-delaying and/or a damping effect.

10. The implantable medical device according to claim 1, further comprising a terminal impedance unit, wherein said switching unit connects a particular function conductor of the plurality of function conductors to said terminal impedance unit.

11. The implantable medical device according to claim 10, wherein said terminal impedance unit comprises at least one impedance value that is controllable.

12. The implantable medical device according to claim 11, wherein said waves are destructively superimposed at the at least one electrode pole via the at least one terminal impedance that is controllable, such that a reflection of the waves is adjusted based on phase position and damping.

* * * * *